US011660198B1

(12) United States Patent
Al-Omran

(10) Patent No.: US 11,660,198 B1
(45) Date of Patent: May 30, 2023

(54) METHOD OF TREATING OSTEOARTHRITIS OF THE KNEE

(71) Applicant: Abdullah Sulaiman Al-Omran, Alkhobar (SA)

(72) Inventor: Abdullah Sulaiman Al-Omran, Alkhobar (SA)

( * ) Notice: Subject to any disclaimer, the term of this patent is extended or adjusted under 35 U.S.C. 154(b) by 5 days.

(21) Appl. No.: 17/969,635

(22) Filed: Oct. 19, 2022

(51) Int. Cl.
  *A61F 2/38* (2006.01)
  *A61B 17/16* (2006.01)
  *A61F 2/28* (2006.01)

(52) U.S. Cl.
  CPC ........ *A61F 2/3877* (2013.01); *A61B 17/1677* (2013.01); *A61F 2/389* (2013.01); *A61F 2/3859* (2013.01); *A61F 2002/285* (2013.01)

(58) Field of Classification Search
  CPC ....... A61F 2/3859; A61F 2/389; A61F 2/3877
  See application file for complete search history.

(56) References Cited

U.S. PATENT DOCUMENTS

2021/0085443 A1* 3/2021 Kocak ...................... A61F 2/12
2021/0330363 A1 10/2021 Robichaud et al.

FOREIGN PATENT DOCUMENTS

CN    209018857    6/2019

OTHER PUBLICATIONS

Asavamongkolkul et al., "Plate Fixation Technique for Reducing Osteoarticular Allograft Fracture: A Preliminary Report," J Med Assoc Thai, vol. 99, No. 10, 2016.

* cited by examiner

Primary Examiner — Jason-Dennis N Stewart
(74) Attorney, Agent, or Firm — Nath, Goldberg & Meyer; Richard C. Litman

(57) ABSTRACT

The method of treating osteoarthritis of the knee (OAK) includes resection of the patella, patellar tendon, proximal tibia, and distal femur, and bone grafting after resection. The bone grafting includes using a single complete osteo-articular allograft configured to replace the knee joint, distal femur, and proximal tibia. Metallic plates are used for internal fixation of the allograft. The procedure can provide patients with full knee flexion, and thereby enable kneeling, e.g., as required in the Islamic prayer.

9 Claims, 1 Drawing Sheet

METHOD OF TREATING OSTEOARTHRITIS OF THE KNEE

BACKGROUND

1. Field

The disclosure of the present patent application relates to a method of treating osteoarthritis of the knee, and particularly, to a method of treating osteoarthritis of the knee by replacing cartilage in the femur and tibia with allograft.

2. Description of the Related Art

Knee osteoarthritis (OA) is the most common, degenerative type of arthritis, and occurs most often in people fifty years of age and older. In osteoarthritis, the cartilage in the knee joint gradually wears away. The incidence of knee OA was 203 per 10,000 persons per year. Correspondingly, there are around annual 86.7 (95% CI, 45.3-141.3) million individuals with incident knee OA in 2020 worldwide.

The four stages of osteoarthritis are: Stage 1 (minor)—associated with minor wear-and-tear in the joints and little to no pain in the affected area; Stage 2 (mild)—associated with more noticeable bone spurs; Stage 3 (moderate)—associated with beginning of erosion of cartilage in the affected area; and Stage 4 (severe)—associated with significant pain.

Management of OA includes weight loss, exercise, pain relievers, anti-inflammatory drugs, injections of corticosteroids or hyaluronic acid into the knee, and alternative therapies using devices (such as braces), physical and occupational therapy, and surgery.

Surgery is reserved for patients whose symptoms have not responded to other treatments. The well-accepted indication for surgery is continued pain and disability despite conservative treatment. The most effective surgical intervention is total knee replacement (TKA), with excellent patient outcomes following total joint replacement of the knee. The complications of TKA are many, including amputations, neurovascular, vascular injury and bleeding, peroneal nerve injury, extensor mechanism, patellar prosthesis loosening, patellar clunk, patellar maltracking, extensor mechanism rupture, periprosthetic infection, periprosthetic fracture, metal hypersensitivity, wound complications, instability (tibio-femoral), stiffness, and infection ending in amputation.

Thus, a method for treating osteoarthritis solving the aforementioned problems is desired.

SUMMARY

The method of treating osteoarthritis of the knee (OAK) includes resection of the patella, patellar tendon, proximal tibia, and distal femur, and bone grafting after resection. The bone grafting includes using a single complete osteo-articular allograft to replace the knee joint, distal femur, and proximal tibia. Metallic plates are used for fixation of the allograft. The procedure can provide patients with full knee flexion, and thereby enable kneeling, e.g., as required in the Islamic prayer.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
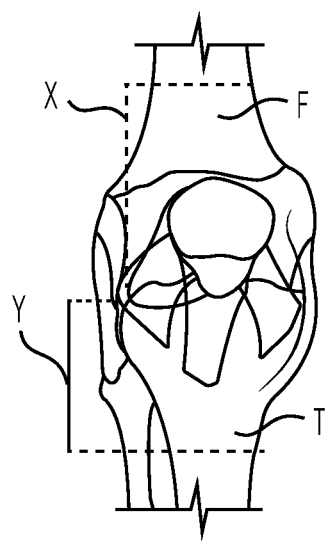
FIG. 1 is a schematic perspective view of the femur and tibia prior to resection with native anterior and posterior cruciate ligaments intact.
Figure 2:
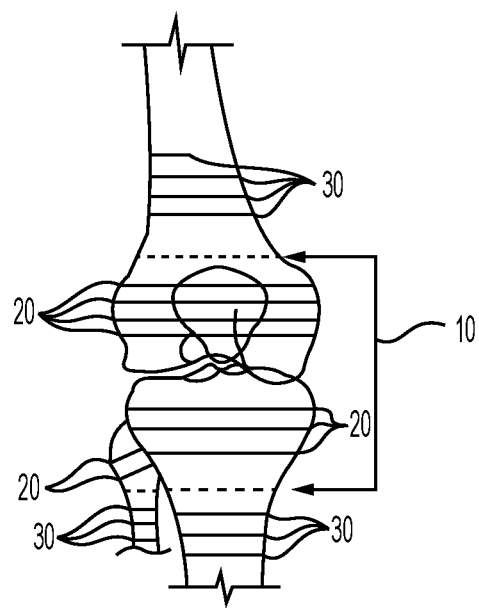
FIG. 2 is a schematic perspective view of the osteoarticular allograft, which includes cartilage and cancellous bone.

The method of treating osteoarthritis of the knee (OAK) includes resection of the patella, patellar tendon, proximal tibia T, and distal femur F (FIG. 1), and bone grafting after resection. The bone grafting includes using a single complete osteo-articular allograft 10 to replace the knee joint, distal femur F, and proximal tibia T (FIG. 2). Metallic plates 20 are used for internal fixation of the allograft 10 (FIG. 2), with three screws above and below the graft for stability. For example, a plurality of lateral dynamic compression plates (DCP) are used for fixation of the allograft 10. Soft tissue suturing is used for suturing the patellar tendon to the native tendon and suturing of the semitendinosis, semimembranosis, and gracilis laterally to the head of the fibula biceps femoris tendon. In an embodiment, the allograft is configured to replace the whole knee capsule with patellar tendon, a portion X of the adjacent femur F, a portion Y of the adjacent tibia T, the native cruciates, the menisci, and the collateral ligaments. In an embodiment, the portion X of the adjacent femur F is about ten centimeters. In an embodiment, the portion Y of the adjacent tibia T is about ten centimeters. The procedure can provide patients with full knee flexion, and thereby enable kneeling, e.g., as required in the Islamic prayer.

In an embodiment, the resection includes resection of the patella and patellar tendon followed by osteotomizing of the tibia and fibula below the tibial tuberosity. The femur F can be osteotomized leaving a margin of five centimeters from the tip of the articular cartilage. Both the tibial and femur allograft edges can carry cancellous bone. This can help to initiate early union and incorporation with the native bone. The plates affixed to the allograft can facilitate sufficient fixation of the allograft to the femur and tibia.

Resection can include making a medial parapatellar incision. Three essential landmarks for the incision include the proximal medial border of the quadriceps tendon, a point halfway between the vastus medialis insertion, and the medial edge of the tibial tubercle. The patella can be everted laterally prior to standard dissection. The patella can be removed with the tendon at the femoral osteotomy.

The allograft is preferably pre-designed and selected based on optimal size and quality using clinical matching radiographs and computerized tomography (CT) scans. Allograft harvesting can be done according to the criteria of the American Association of Tissue Banks, in sterile conditions followed by irradiating the tissue at 25,000 Gy and stored at −70° C. The allograft can be thawed in warm saline water.

Initial sizing of the allograft can be based on computerized tomography. The allograft includes the knee joint, the distal femur and proximal tibia. Preferably, the allograft is designed to replace the whole capsule with patellar tendon, at least ten centimeters of the adjacent tibia, fibula and femur, as well as native cruciates, menisci, and collateral ligaments. A tibial component of the allograft can replace about fourteen millimeters of the proximal tibia Exact cuts can be made on the allograft based on the size of the patient's knee joint. After careful measurement of the allograft, additional cuts can be made on the native bones to accommodate the allograft so that limb length discrepancy can be avoided. The complete allograft with distal femur, proximal tibia, medial and lateral menisci, as well as native anterior and posterior cruciate ligaments can then be transplanted to the affected knee. The allograft can be fixed to the femur and the tibia using the DCPs as shown in FIG. 2.

Preferably, the tibia is prepared first. The patellar tendon is detached from the tibial tuberosity and deflected upwards. The tibia and fibula can be osteotomized below the tibial tuberosity, while taking care to avoid injury to the common peroneal nerve running close to the neck of the fibula and detaching laterally the fascia lata, the tendons of semitendinosis, semimembranosis, and gracilis to allow subsequent re-attachment. The posterior structure of the neuro-vascular bundle should be avoided. The tibial rotation is based on the tibial tubercle, with the allograft being held using K wires and affixed subcutaneously using lateral dynamic compression plates (DCP).

The femur can be osteotomized with a five centimeter margin from the tip of the articular cartilage. In preparing the femur, the allograft is positioned and matched for rotation and height, fixed with "k" wires initially, and then with lateral DCPs 20 subcutaneously. Soft tissue suturing 30 can then be used for suturing the patellar tendon to the native tendon and suturing of the semitendinosis, semimembranosis, and gracilis laterally to the head of the fibula biceps femoris tendon. The head of the fibula can be secured with two screws.

Post-operatively, the patient can receive antibiotics for a week and anti-thrombotic medication for four weeks. The initial postoperative visit can occur approximately two weeks after surgery. Sutures can be removed within fourteen days after surgery. The wound can then be checked, along with range of motion and ambulatory ability. Postoperative radiographs including a standing AP, lateral, and skyline view can be obtained. Rehabilitation protocols continue to evolve and accelerate. Patients begin ambulation the day of surgery, with partial weight bearing. A knee immobilizer can be applied at night to maintain extension and provide comfort for transfers and initial ambulation the day of surgery. Weight-bearing for distances can be protected with crutches or a walker for eight weeks. All support can be discontinued at twelve weeks once the union to the native bone occurs with the allograft based on serial radiographs.

It is to be understood that the method for treating osteoarthritis of the knee is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating osteoarthritis of the knee of a patient in need thereof, the patient's knee including a patella, patellar tendon, proximal tibia, and distal femur, the method comprising the steps of:
   resecting the patella and patellar tendon;
   osteotomizing the tibia and fibula;
   osteotomizing the femur;
   replacing the knee joint, distal femur, and proximal tibia using an osteo-articular allograft having cancellous bone along an edge thereof; and
   placing a plurality of dynamic compression plates for internal fixation of the osteo-articular allograft.

2. The method of treating osteoarthritis of the knee according to claim 1, wherein at least ten centimeters of the tibia and femur are replaced by the osteo-articular allograft.

3. The method of treating osteoarthritis of the knee according to claim 1, wherein the osteo-articular allograft further replaces the native cruciates, the menisci, and collateral ligaments of the patient's knee.

4. The method of treating osteoarthritis of the knee according to claim 1, wherein osteotomizing the femur comprises leaving a five centimeter margin from the tip of the articular cartilage.

5. The method of treating osteoarthritis of the knee of claim 1, wherein a tibial component of the allograft replaces about fourteen millimeters of the proximal tibia.

6. The method of treating osteoarthritis of the knee of claim 1, wherein the tibia and fibula are osteotomized below the tibial tuberosity.

7. The method of treating osteoarthritis of the knee of claim 1, wherein the internal fixation comprises lateral, subcutaneous fixation.

8. A method of treating osteoarthritis of the knee of a patient in need thereof, the patient's knee including a patella and patellar tendon, proximal tibia, and distal femur, the method comprising the steps of:
   resecting the patella and patellar tendon;
   osteotomizing the tibia and fibula below the tibial tuberosity;
   osteotomizing the femur;
   replacing the knee joint, at least ten centimeters of the distal femur, and at least ten centimeters of the proximal tibia using an osteo-articular allograft having cancellous bone along an edge thereof; and
   placing a plurality of dynamic compression plates for lateral, subcutaneous fixation of the allograft.

9. The method of treating osteoarthritis of the knee according to claim 8, wherein the step of osteotomizing the femur comprises leaving a five centimeter margin from the tip of the articular cartilage.

* * * * *